United States Patent
Harder et al.

Patent Number: 5,969,885
Date of Patent: Oct. 19, 1999

[54] SYSTEM AND APPARATUS FOR CALIBRATING AN IMAGE DETECTOR

[75] Inventors: James A. Harder, Bedford; Keith A. Jacobson, Flower Mound; Val J. Herrera, Double Oak, all of Tex.

[73] Assignee: Raytheon Company, Lexington, Mass.

[21] Appl. No.: 08/969,069

[22] Filed: Nov. 12, 1997

Related U.S. Application Data

[62] Division of application No. 08/741,875, Oct. 30, 1996, Pat. No. 5,705,811
[60] Provisional application No. 60/007,132, Oct. 31, 1995.
[51] Int. Cl.⁶ .................................................. G02B 7/02
[52] U.S. Cl. ........................................ 359/811; 359/822
[58] Field of Search ..................................... 359/822, 811

[56] References Cited

U.S. PATENT DOCUMENTS

| | | | |
|---|---|---|---|
| 5,422,485 | 6/1995 | Bowlds | 250/252.1 |
| 5,576,897 | 11/1996 | Kuo | 359/822 |

*Primary Examiner*—Georgia Epps
*Assistant Examiner*—Michael A. Lucas
*Attorney, Agent, or Firm*—Baker & Botts, L.L.P.

[57] ABSTRACT

A system (10) for calibrating an image detector includes a calibration platform (16) supporting a calibration element (18). The calibration element (18) may be made up of a first portion (20) and a second portion (22), each having a curved surface (20A, 22A) to appropriately alter characteristics of reference light levels (33) generated by a reference source (24). The second portion (22) may have its surface positioned differently to the focal plane array (14) than the first portion (20) for enhanced calibration operation. The reference source (24) generates the reference light levels (33) over a range of temperatures to mimic the image energy generated by the scene (12). The reference source (24) may also include a reference portion element (26) that transmits reference light energy (33) generated by the reference source (24) or reflects scene base energy (34) generated by the scene (12) and allowed to pass through the first portion (20) and the second portion (22). The calibration platform (16) operates to position the first portion (20) and the second portion (22) in front of the focal plane array (14) during calibration operation and remove the first portion (20) and the second portion (22) from in front of the focal plane array (14) during normal image detection.

14 Claims, 1 Drawing Sheet

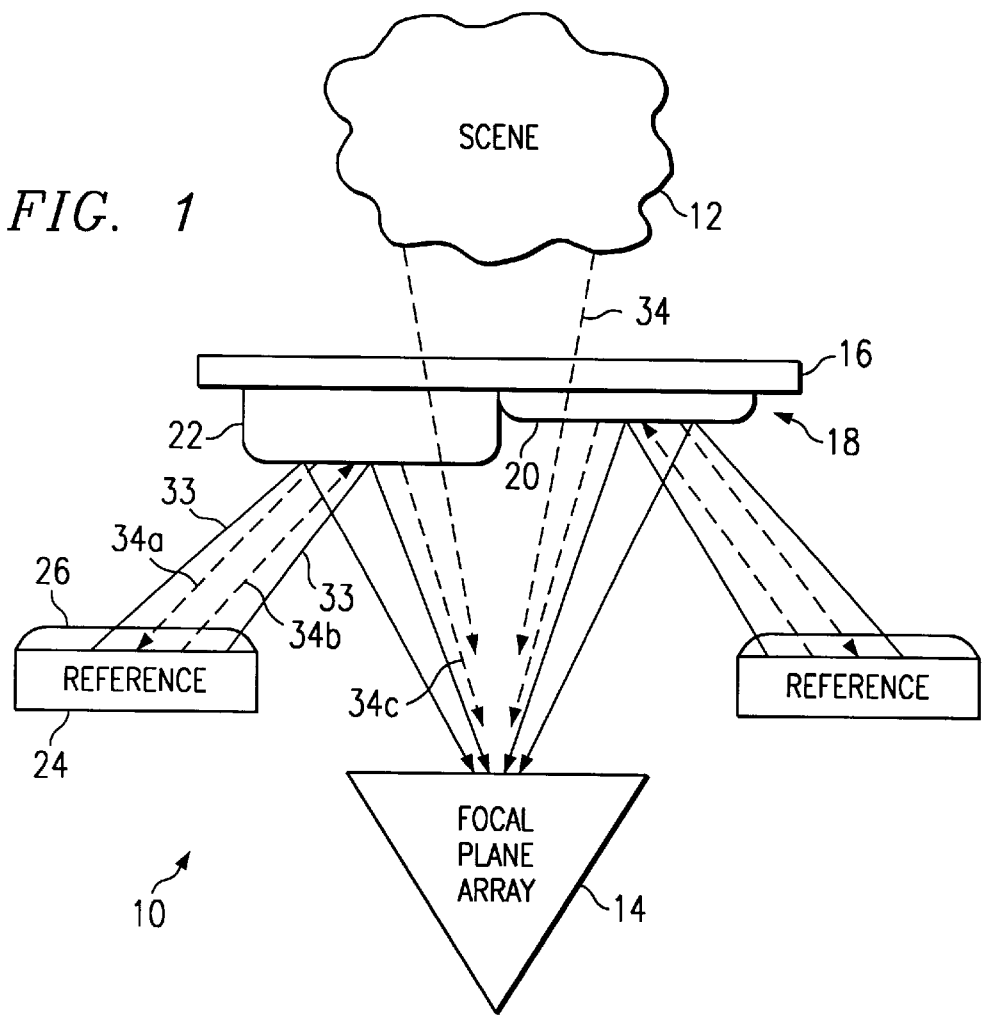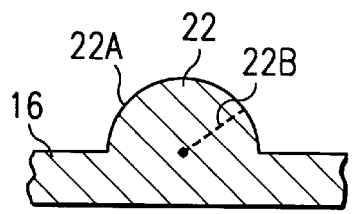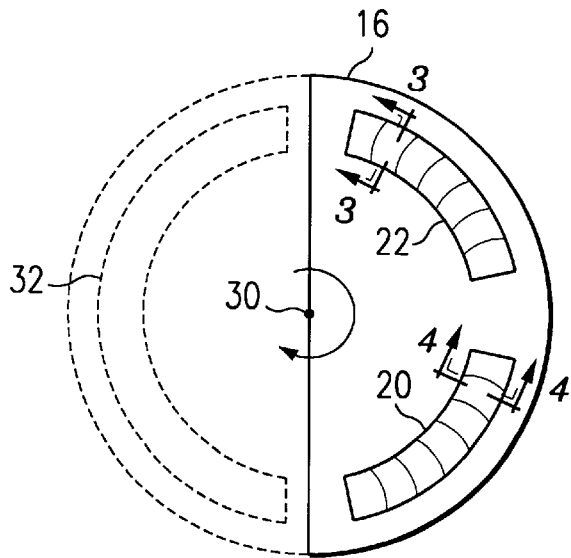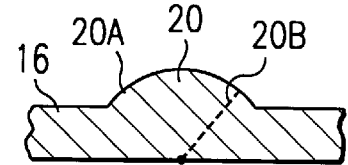

SYSTEM AND APPARATUS FOR CALIBRATING AN IMAGE DETECTOR

CROSS REFERENCE TO RELATED APPLICATIONS

This application is a divisional of U.S. application Ser. No. 08/741,875 filed Oct. 30, 1996 now U.S. Pat. No. 5,705,811 by James A. Harder, Keith A. Jacobson and Val J. Herrera entitled "System and Apparatus for Calibrating an Image Detector," which claims priority to provisional application Ser. No. 60/007,132, filed Oct. 31, 1995, and entitled "System and Apparatus for Calibrating an Image Detector."

TECHNICAL FIELD OF THE INVENTION

The present invention relates in general to imaging detection technology and more particularly to a system and apparatus for calibrating an image detector.

BACKGROUND OF THE INVENTION

Calibration of focal plane arrays in image detection systems is necessary to adequately detect images within a scene. Typical opto-mechanical calibration techniques include using a shutter to flash in front of the focal plane array during calibration. The shutter may include a specific reference image such that the focal plane array detects a specific reference in order to calibrate its image sensing devices. The shutter may include a flat mirror such that the focal plane array detects itself for calibration purposes. The shutter/flat mirror technique only allows the focal plane array to calibrate on itself or a specific reference. Therefore, imaging system can benefit from improved opto-mechanical calibration schemes.

SUMMARY OF THE INVENTION

From the foregoing, it may be appreciated that a need has arisen for an improved and effective system and apparatus for calibrating an image detector. In accordance with the present invention, a system and apparatus for calibrating an image detector are provided that substantially eliminate or reduce disadvantages and problems associated with conventional image detector calibration techniques.

According to an embodiment of the present invention, there is provided a system for calibrating an image detector that includes a focal plane array operable to detect images from a scene. A reference source generates reference light levels to a movable calibration platform. The reference light levels are reflected and/or refracted from the movable calibration platform to the focal plane array. The movable calibration platform may include a calibration portion with a curved surface for reflecting the reference light levels.

The present invention provides various technical advantages over conventional image detector calibration techniques. For example, one technical advantage is to use a curved surface for calibration of a focal plane array. Another technical advantage is to allow scene based energy to be used in the calibration of the focal plane array. Yet another technical advantage is to generate reference light levels to mimic the scene energy in order to produce the calibration references that best match scene conditions. Still another technical advantage is to mix reference light levels with scene based energy for calibration of the focal plane array. Other technical advantages are readily apparent to one skilled in the art from the following figures, descriptions, and claims.

BRIEF DESCRIPTION OF THE DRAWINGS

For a more complete understanding of the present invention and the advantages thereof, reference is now made to the following description taken in conjunction with the accompanying drawings, wherein like reference numerals represent like parts, in which:

FIG. 1 illustrates a system for calibrating an image detector;

FIG. 2 illustrates a calibration platform for use in the image detector calibration system;

FIG. 3 is a sectional view taken along the line 3—3 in FIG. 2; and

FIG. 4 is a sectional view taken along the line 4—4 in FIG. 2.

DETAILED DESCRIPTION OF THE INVENTION

FIG. 1 is a simplified diagram of a system 10 for calibrating an image detector. System 10 receives energy from a scene 12 at a focal plane array 14. Focal plane array 14 processes energy received from scene 12 in order to detect an image of scene 12. System 10 also includes a calibration platform 16 that is positioned in front of focal plane array 14 for calibration of system 10. Calibration platform 16 includes a calibration element 18 having a first portion 20 and a second portion 22. System 10 also includes a reference source 24 that generates reference light levels for the calibration of focal plane array 14. Reference source 24 may also include a reference lens element 26 to control reference light levels generated by reference source 24. Reference portion element 26, first portion 20, and second portion 22 may be lenses having partial or total reflective surfaces, may be mirrors, or may allow partial or complete transmission of light depending upon the form of calibration desired.

For normal operation, calibration platform 16 is removed from in front of focal plane array 14 to allow focal plane array 14 to collect scene image levels 34 directly from scene 12. During calibration of system 10, calibration platform 16 is positioned in front of focal plane array 14. Reference source 24 is activated to generate reference light levels 33 that reflect from calibration element 18 for processing by focal plane array 14. Calibration platform 16 can be positioned in front of focal plane array 14 on a periodic or a periodic basis to provide continuous or on demand calibration of focal plane array 14.

Reference source 24 may include a thermo-electric cooler/heater that can generate a range of temperatures to produce reference light levels 33. The temperature generated by reference source 24 may be passively set to a specific value or activity controlled to match the temperature at scene 12. The purpose of reference source 24 working in conjunction with calibration platform 16 is to apply passively and/or actively controlled spatially conditioned photons to focal plane array 14 and avoid photon gathering from unwanted places within system 10. Reference source 24 may implement reference portion element 26 to direct reference light levels 33 to calibration element 18.

Reference portion element 26 may direct scene image levels 34 (34a) refracted through calibration element 18 with a reflective surface back towards calibration element 18 (34b) for reflection to focal plane array 14 (34c). Reference portion element 26 may also allow transmission of reference light levels 33 therethrough as generated by reference source 24 for reflection from calibration element 18 to focal plane array 14. The net result of operating calibration element 18 with reference portion element 26 and reference source 24 is a temporal and spatially controlled mixing of scene energy 34 and reference energy 33. This mixing provides an optimized photon reference for focal plane array 14.

FIG. 2 is a simplified diagram of calibration platform 16. In this implementation, calibration platform 16 preferably rotates around an axis 30. Rotation of calibration platform 16 around axis 30 allows for the positioning of first portion 20 and second portion 22 in front of focal plane array 14 during calibration. For image detection, calibration platform 16 rotates to remove first portion 20 and second portion 20 from in front of focal plane array 14. Though shown as a half disk, calibration platform 16 may have a full disk configuration as indicated by the dashed lines with an aperture 32 that can be rotated to a position in front of focal plane array 14 for image detection operation.

First portion 20 and second portion 22 preferably have curved surfaces 20A (FIG. 4) and 22A (FIG. 3) in order to alter the characteristic of reference light levels 33 generated by reference source 24. The curved surfaces of first portion 20 and second portion 22 are selected to appropriately alter the characteristics of reference light levels 33 reflected toward focal plane array 14. The curved surface 20A has a radius of curvature 20B (FIG. 4) and the curved surfaces 22A has a radius of curvature 22B (FIG. 3). Due to the fact that each of the surfaces 20A and 22A is defined by a respective radius of curvature, the surface 20A thus has an optical reflecting characteristic which is uniform at all locations therealong, and the surface 22A has a different optical reflecting characteristic which is uniform at all locations therealong. In addition to reflecting reference light levels 33 from reference source 24, first portion 20 and second portion 22 may allow energy 34 from scene 12 to be applied directly to focal plane array 14 and/or indirectly by reflection from reference portion element 26 at reference source 24. In this manner, scene based energy 34 may be used for the calibration of focal plane array 14. Further, first portion 20 may have its surface 20A spaced from focal plane array 14 at a different distance and orientation than the surface 22A of second portion 22. Different displacements of first portion 20 and second portion 22 from focal plane array 14 provide different and additional parameters for calibration of focal plane array 14.

Opto-mechanical characteristics of first portion 20 and second portion 22 may be altered in order to affect an amount of transmittance or reflectance of scene based energy 34 and/or reference light levels 33. Opto-mechanical a characteristics include different portion orientations, selective coating on the lenses, and selective patterning of the lenses. With changes to the opto-mechanical characteristics of the portion 20 and 22, variable mixing of scene based energy 34 and reference light levels 33 may be achieved for selective calibration performance.

In summary, a system for calibrating an image detector includes a calibration platform having a calibration portion element made up of a first portion and a second portion. The first portion and the second portion direct reference light levels generated by a reference source to a focal plane array in order to calibrate the focal plane array. The first portion and the second portion have curved surfaces with selected transmittance and reflectance levels to alter the characteristics of the reference light levels for appropriate calibration purposes. The first portion and the second portion may have surfaces at different distances and orientations to the focal plane array. The reference source generates reference light levels through a range of different temperatures or through reflection and transmission by a reference portion element. The calibration platform positions the calibration portion element in front of the focal plane array during calibration operation and removes the calibration portion element from in front of the focal plane array during image detection of a scene.

Thus, it is apparent that there has been provided, in accordance with the present invention, a system for calibrating an image detector that satisfies the advantages set forth above. Although the preferred embodiment has been described in detail, it should be understood that various changes, substitutions, and alterations can be made herein. For example, though the calibration platform is shown to rotate the first portion and the second portion into position for calibration purposes, the first and second portions may be positioned in front of the focal plane array by a variety of placement techniques not limited by rotary motion. Other examples are readily ascertainable by one skilled in the art and may be made without departing from the spirit and scope of the present invention as defined by the following claims.

What is claimed is:

1. A calibration element for calibrating an image detector, comprising:

a movable base;

a first optical portion on said movable base, said first optical portion having a curved surface;

a second optical portion on said movable base, said second optical portion having a curved surface, said curved surface of said second optical portion extending a distance away from said movable base different than said curved surface of said first optical portion.

2. A calibration element, comprising: a base; and an elongate optical portion which is provided on said base and extends in a direction, said optical portion effecting redirection of radiation impinging thereon according to a characteristic which is substantially uniform at all locations along the length of said optical portion.

3. A calibration element according to claim 2, wherein said direction extends concentrically to an axis of rotation for said base.

4. A apparatus according to claim 3, wherein said base has therethrough an elongate aperture which extends in said direction, said aperture being spaced in said direction from said optical portion.

5. A calibration element according to claim 2, wherein said optical portion has thereon a reflective surface which has a uniform cross-sectional shape at all locations along the length of said optical portion.

6. A calibration element according to claim 2, wherein said optical portion is a lens which has a uniform cross-sectional shape at all locations along the length of said optical portion.

7. A calibration element, comprising: a base; and elongate first and second optical portions which are each provided on said base at respective positions spaced from each other in a direction, said optical portions each extending in said direction, said first optical portion effecting redirection of radiation impinging thereon according to a first characteristic which is substantially uniform at all locations along the length of said first optical portion, and said second optical portion effecting redirection of radiation impinging thereon according to a second optical characteristic which is substantially uniform at all locations along the length of said second optical portion, said second characteristic being different from said first characteristic.

8. A calibration element according to claim 7, wherein said direction extends concentrically to an axis of rotation for said base.

9. A calibration element according to claim 8, wherein said base has therethrough an elongate aperture which extends in said direction, said aperture being spaced in said direction from each of said first and second optical portions.

10. A calibration element according to claim 8, wherein said base is disposed on one side of said axis, and said axis is disposed in the region of one edge of said base.

11. A calibration element according to claim 7, wherein said first optical portion has thereon a first reflective surface which has a uniform cross-sectional shape at all locations along the length of said first optical portion, and wherein said second optical portion has thereon a second reflective surface which has a uniform cross-sectional shape at all locations along the length of said second optical portion.

12. A calibration element according to claim 11, wherein said first and second reflective surfaces each have an arcuate cross-sectional shape, said first reflective surface having a first radius, and said second reflective surface having a second radius which is different from said first radius.

13. A calibration element according to claim 7, wherein said first and second optical portions are each a lens which has a uniform cross-sectional shape at all locations along the length thereof.

14. A calibration element according to claim 7, wherein said first optical portion has a first surface thereon which faces generally in a further direction approximately perpendicular to said direction in which said first and second optical portions extend, and wherein said second optical portion has a second surface thereon which faces generally in said further direction, said first surface being offset in said further direction relative to said second surface.

* * * * *